(12) United States Patent
Mishra et al.

(10) Patent No.: US 9,943,575 B2
(45) Date of Patent: Apr. 17, 2018

(54) PHARMACEUTICAL COMPOSITIONS OF TENECTEPLASE

(71) Applicant: Gennova Biopharmaceuticals Limited, Pune (IN)

(72) Inventors: Maheshwari Kumar Mishra, Pune (IN); Pritiranjan Bhandari, Pune (IN); Sanjay Singh, Pune (IN)

(73) Assignee: Gennova Biopharmaceuticals Limited, Pune (IN)

( * ) Notice: Subject to any disclaimer, the term of this patent is extended or adjusted under 35 U.S.C. 154(b) by 0 days.

(21) Appl. No.: 15/136,614

(22) Filed: Apr. 22, 2016

(65) Prior Publication Data

US 2016/0310580 A1 Oct. 27, 2016

Related U.S. Application Data

(62) Division of application No. 13/993,297, filed as application No. PCT/IN2011/000863 on Dec. 16, 2011, now abandoned.

(30) Foreign Application Priority Data

Dec. 23, 2010 (IN) .................. 3516/MUM/2010

(51) Int. Cl.
| | |
|---|---|
| *A61K 38/48* | (2006.01) |
| *A61K 9/00* | (2006.01) |
| *A61K 9/19* | (2006.01) |
| *A61K 47/02* | (2006.01) |
| *A61K 47/18* | (2017.01) |
| *A61K 47/26* | (2006.01) |

(52) U.S. Cl.
CPC .......... *A61K 38/482* (2013.01); *A61K 9/0019* (2013.01); *A61K 9/19* (2013.01); *A61K 47/02* (2013.01); *A61K 47/183* (2013.01); *A61K 47/26* (2013.01); *C12Y 304/21068* (2013.01)

(58) Field of Classification Search
None
See application file for complete search history.

(56) References Cited

U.S. PATENT DOCUMENTS

| | | | |
|---|---|---|---|
| 2007/0014779 A1 | 1/2007 | Semba | |
| 2008/0107641 A1* | 5/2008 | Kuebler | ............... A61K 9/0019 424/130.1 |
| 2010/0184149 A1 | 7/2010 | Laustsen | |
| 2010/0330083 A1 | 12/2010 | Semba | |

FOREIGN PATENT DOCUMENTS

| | | |
|---|---|---|
| WO | WO-2008027687 A2 | 3/2008 |
| WO | WO-2008070353 A2 | 6/2008 |
| WO | WO-2008152075 A1 | 12/2008 |

OTHER PUBLICATIONS

Genentech, Inc., TNKase Dosing Sheet; Genentech, Inc.: South San Francisco, CA, 2005.*
International Search Report issued in PCT/IN2011/000863 dated May 31, 2012.
Jiang, et al., Characterization of the Glycosylation Occupancy and the Active Site in the Follow-on Protein Therapeutic: TNK-Tissue Plasminogen Activator, Analytical Chemistry, 2010, 82:6154-6162.
Haley, et al., Stroke, 36:607-12, 2005.
Haley, et al., Stroke, 41(4):707-711, 2010.
Parsons, et al., N. Engl. J. Med., 366(12):1099-1107, 2012.

* cited by examiner

*Primary Examiner* — Michelle F. Paguio Frising
(74) *Attorney, Agent, or Firm* — Blank Rome LLP (57) ABSTRACT

Pharmaceutical compositions of tenecteplase that are safe and effective in the treatment of acute ischemic stroke compared with the known compositions are disclosed. The compositions of the invention are invented based on a series of testing trials on the different amounts of the TNK and isolating specific amount that is optimally suitable in terms of desired effects of TNK in the treatment of acute ischemic stroke.

15 Claims, 4 Drawing Sheets

SEQUENCE LISTING

<160> NUMBER OF SEQ ID NOS: 1

<210> SEQ ID NO 1
<211> LENGTH: 562
<212> TYPE: PRT
<213> ORGANISM: Homo sapiens

<400> SEQUENCE: 1

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ser Tyr Gln Val Ile Cys Arg Asp Glu Lys Thr Gln Met
            35                  40                  45

Ile Tyr Gln Gln His Gln Ser Trp Leu Arg Pro Val Leu Arg Ser Asn
        50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110
```

-continued

Gly Phe Ala Gly Lys Cys Cys Glu Ile Asp Thr Arg Ala Thr Cys Tyr
                115                 120                 125

Glu Asp Gln Gly Ile Ser Tyr Arg Gly Thr Trp Ser Thr Ala Glu Ser
130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
                180                 185                 190

Phe Lys Ala Gly Lys Tyr Ser Ser Glu Phe Cys Ser Thr Pro Ala Cys
                195                 200                 205

Ser Glu Gly Asn Ser Asp Cys Tyr Phe Gly Asn Gly Ser Ala Tyr Arg
                210                 215                 220

Gly Thr His Ser Leu Thr Glu Ser Gly Ala Ser Cys Leu Pro Trp Asn
225                 230                 235                 240

Ser Met Ile Leu Ile Gly Asn Val Tyr Thr Ala Gln Asn Pro Ser Ala
                245                 250                 255

Gln Ala Leu Gly Leu Gly Lys His Asn Tyr Cys Arg Asn Pro Asp Gly
                260                 265                 270

Asp Ala Lys Pro Trp Cys His Val Leu Lys Asn Arg Arg Leu Thr Trp
                275                 280                 285

Glu Tyr Cys Asp Val Pro Ser Cys Ser Thr Cys Gly Leu Arg Gln Tyr
                290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
                340                 345                 350

Leu Ser Ala Ala His Cys Phe Gln Glu Arg Phe Pro Pro His His Leu
                355                 360                 365

Thr Val Ile Leu Gly Arg Thr Tyr Arg Val Val Pro Gly Glu Glu Glu
                370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
                420                 425                 430

Pro Ala Asp Leu Gln Leu Pro Asp Trp Thr Glu Cys Glu Leu Ser Gly
                435                 440                 445

Tyr Gly Lys His Glu Ala Leu Ser Pro Phe Tyr Ser Glu Arg Leu Lys
                450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
                500                 505                 510

Ser Gly Gly Pro Leu Val Cys Leu Asn Asp Gly Arg Met Thr Leu Val
                515                 520                 525

Gly Ile Ile Ser Trp Gly Leu Gly Cys Gly Gln Lys Asp Val Pro Gly

-continued

```
                530                 535                 540
Val Tyr Thr Lys Val Thr Asn Tyr Leu Asp Trp Ile Arg Asp Asn Met
545                 550                 555                 560

Arg Pro
```

PHARMACEUTICAL COMPOSITIONS OF TENECTEPLASE

This application is a divisional of U.S. patent application Ser. No. 13/993,297, filed Jul. 26, 2013, which is the U.S. national phase of International Patent Application No. PCT/IN2011/000863, filed Dec. 16, 2011, which claims the benefit of Indian Patent Application No. 3516/MUM/2010, filed Dec. 23, 2010, each of which is hereby incorporated by reference.

SEQUENCE LISTING

The instant application contains a Sequence Listing which has been submitted electronically in ASCII format and is hereby incorporated by reference in its entirety. The ASCII copy, created on Jul. 6, 2016, is named 141466_01001 SL.txt and is 5,214 bytes in size.

FIELD OF THE INVENTION

This invention relates to the pharmaceutical compositions of a derivative of human tissue plasminogen activator known as tenecteplase (TNK) for the treatment of blockage of the cerebral arteries that cause strokes of major or minor types such as acute ischemic stroke (AIS). The invention also relates to the formulations having optimal efficacy and safety compared with the known therapy agents as identified in clinical trials of the said compositions with specific amounts of TNK as active ingredient.

BACKGROUND OF THE INVENTION

Tissue plasminogen activator (TPA) is involved in the breakdown of non-specific blood clots in the blood circulation system. TNK is a derivative of TPA in which seven amino acids of the native sequence are modified so that the new molecule has changed specificity to the fibrin protein and changed pharmacokinetic properties leading to changed pharmacodynamic effects. TNK is a 527-amino acid glycoprotein of molecular weight of 70 KDa. It has been approved for use in the medicinal products for the treatment of acute myocardial infarction and some other thrombosis and embolism related breakage of blood vessels in different organs. Recently, it has been considered for the treatment of acute ischemic stroke and several clinical trials have been performed for this indication, but these trials have not given any conclusive evidence on the safe and effective dose of TNK for AIS.

Plasminogen activators are enzymes that activate the plasminogen to generate the serine protease plasmin that in turn degrades fibrin. Among the plasminogen activators used as drugs are: a) streptokinase [a bacterial protein], b) urokinase, [an enzyme synthesized in the kidney] and c) human tissue plasminogen activator [an enzyme produced by the vascular endothelium]. There are also other enzymes in development that are potential candidates as fibrinolytic drugs. The mechanisms of action of these activators differ: streptokinase forms a complex with plasminogen generating plasmin activity, urokinase cleaves plasminogen directly, and TPA forms a ternary complex with fibrin and plasminogen leading to plasminogen activation and clot dissolution in situ. Natural human TPA has a plasma half-life typically of 8-10 minutes. However, it was desired to have increased half-life so that the fibrinolytic therapy may be administrated effectively in a short period of time, with more beneficial efficacy outcomes. Therefore, several amino acid and deletion mutants of the protein were created and tested for the improved characters over TPA. TNK has six mutations that doubled half-life [to 20-24 min.] compared to tPA and improved characters such as higher fibrin clot specificity with concurrent less affinity for plasminogen activator inhibitor-1.

TNK was first disclosed in U.S. Pat. No. 5,385,732 wherein it was produced by recombinant DNA technology using an established mammalian cell line. Several other patents cover different aspects of the production and use of TNK, viz., U.S. Pat. No. 5,728,567, U.S. Pat. No. 5,714,145, U.S. Pat. No. 5,366,886, U.S. Pat. No. 5,094,953, U.S. Pat. No. 5,407,819 and U.S. Pat. No. 6,506,598. U.S. Pat. No. 5,407,819 discloses a method of the preparation of a TPA variant by displacement of a particular amino acid in the amino acid sequence. U.S. Pat. No. 5,612,029 discloses a variant of TPA, which is glycosylated at any positions on 103-105 and devoid of functional carbohydrate structure at position 117 of wild type human TPA sequence. U.S. Pat. No. 5,520,911 discloses the preparation of DNA sequences to encode the TPA variant. U.S. Pat. No. 5,424,198 discloses a method for the production of TPA by transforming the cells with mutant or wild-type DHFR genes in combination with tPA genes. These and several other documents also cover the various medical conditions or indications where TNK can be used as a drug for the treatment related to clot formation. One of the conditions covered by the US20080107641 is AIS. However, this application does not disclose any method of identifying a safe and effective dose of TNK for the treatment of AIS in human subjects. Instead it predicts the use of safe dose based on theoretical models of existing data matrices without giving any specific method of testing and qualifying the identified effective doses. Therefore, current prior art fails to address the unmet need for identification of safe and effective doses of TNK for the treatment of AIS and effective pharmaceutical compositions (formulations) for the treatment of AIS. The present invention addresses the above mentioned need and provides improved and more effective formulations of TNK for the treatment of AIS in human subjects, which is safe as well as easy to administer in a short period of time.

There are some studies that mention the use of TNK for the treatment of AIS, however, they fail to disclose any formulation of TNK with the amounts of TNK that are safe and effective as disclosed herein vis-à-vis its side effects. Besides, the TNK used for the preparation of formulations is prepared using the new technology of perfusion-based continuous fermentation system has not been used previously to prepare the TNK protein.

Various formulations are known that use TNK for the treatment of the AIS. However, so far none has been approved by any drug regulator that is safe and efficacious when vetted on risk-benefit analysis. Having identified this gap, some formulations of TNK are disclosed herein that have desired properties required of a safe and effective drug for the treatment of AIS. Some aspects of the method used in the present disclosure for the preparation of the TNK of high purity are known in the prior art. However, several new elements are used here that are not known in the art for the production, preparation, selection, testing and especially clinical qualification of the formulations of TNK for the treatment of AIS.

OBJECTS OF THE INVENTION

The principal object of the invention is to identify the effective and safe amount of the TNK for the treatment of AIS in human subjects. Another object of the invention is to develop the formulations of TNK that are safe and effective in treatment of AIS in human subjects. Yet another object of the invention is to perform clinical trials to identify the amount of TNK that is safe and effective for the treatment of AIS. A further object of the invention is to use perfusion-based fermentation technology for the recombinant production of TNK used to achieve the above objects.

SUMMARY

The production of TNK was done by recombinant DNA technology in Chinese Hamster Ovary (CHO) cells in a perfusion-based continuous fermentation system. This method affords a large-scale production of the protein with higher quality and quantity, besides being scalable for industrial applications. The recombinant cell line producing TNK as a secreted protein was prepared and selected for the desired nature of TNK, and used for the formulations of TNK for treatment of AIS in human subjects. These formulations having different amounts of TNK were tested in a clinical setting to identify the safe and effective amount of TNK required for optimal treatment of AIS in human subjects. The clinical trial data that provided the amount of TNK which is safe and efficacious for the treatment of AIS is disclosed in the intervention. And the TNK is prepared using perfusion-based continuous fermentation system. In the first part, mammalian cell lines (CHO) was prepared using molecular and cell biological techniques. These cell lines were then screened for expression level of secreted TNK and a highly TNK expressing cell line was isolated for further process development for the pharmaceutical grade TNK production. In the second part, the TNK producing cells were grown in a perfusion-based continuous fermentation system for large-scale production of TNK and collected spent media stored for further processing. In the third part, the harvest was subject to the chromatographic steps to obtain highly pure and potent TNK bulk as active ingredient for the further preparation of the formulations for clinical applications. In the fourth part, a set of formulations of the TNK were prepared and studied for various parameters like stability, potency and other pharmacologic properties in bioassays. In the fifth part, the formulations of TNK prepared were examined in clinical testing to identify the safe and effective amount of TNK required for the treatment of AIS in affected subjects under certain conditions. These studies identified a set of parameters required for the safe and effective use of TNK for the treatment of AIS in the form of injectable formulations.

DETAILED DESCRIPTION

It is known to the skilled person in medicine and pharmacology that in order to obtain safe and effective pharmaceutical compositions, it is a good strategy to develop several formulations of the active ingredient strength with different excipients and test it in desired conditions so that a safe and effective dose of a new drug for specific indication can be identified. The role of excipients is important as they provide additional characters like stability, ease of delivery, volume, etc. The principal object of this invention is to develop an improved preparation of TNK for use as pharmaceutical compositions for the treatment of acute ischemic stroke in human subjects that is safe and efficacious over known formulations. Another object of this invention relates to the use of clinical tests using specific amounts of TNK to determine the safe and effective amount of TNK in the treatment of AIS. Furthermore, there remains a lack of understanding regarding many aspects of recombinant DNA technology, process development and production that affect the productivity and characteristics of the final products. Therefore, there is a need for new methods of preparation of rDNA technology products that are improved over the existing methods and technologies. The objective of this invention is to develop safe and effective pharmaceutical compositions/formulations for the treatment of acute ischemic stroke in human, wherein TNK is produced from a CHO cell line developed de novo and used in a perfusion-based continuous fermentation system for the large-scale production of TNK.

In the first part, the CHO cell line expressing TNK as a secreted protein at a higher level was prepared. Molecular biology, biochemistry and analytical techniques used are standard in the art and have been routinely used. The mammalian expression plasmid used for the creation of the expression cell line contained a CMV promoter/enhancer element before an artificial gene of TNK followed by a SV40 poly-A tail for transcription termination. The same plasmid also contained a DHFR gene under the control of SV40 promoter, ending with a SV40 poly-A tail. This plasmid was transfected to CHO cells negative for the native DHFR gene (CHO-DHFR-cell line). One cell line with higher levels of TNK expression was isolated and further used [Example 1 and 2].

In the second part, the TNK-expressing CHO cells were used for the large-scale preparation of TNK in perfusion-based continuous fermentation system. About $6\text{-}12\times10^9$ cells were immobilised in the reactor core of the perfusion bioreactor. These cells were allowed to grow in IMDM medium with FBS for about for a few days till the required cell mass developed under constant glucose concentration of about 1-2 gm/L in chemostatic mode. During production phase, the medium was changed to CHO-S-SFM II without FBS, and fermentation continued for several months under glucose fed conditions while a certain concentration of crude TNK product was produced in the harvested medium for further downstream processing. The harvest media was collected in sterile containers and stored at 4° C. till further use in subsequent purification steps [Examples 3, 5 and 7].

In the third part, the harvested medium containing crude TNK were subjected to a set of the chromatographic steps in a series. This included a dye-affinity capture step, followed by lysine-affinity purification step and a final ion exchange polishing step. Table A depicts different steps of the chromatographic purification leading to several fold increase in the amount of the purified protein as determined by SDS-PAGE densitometry/HPSEC. Before subjecting the harvested broth to the purification process it contained about 80% TNK protein. At the end of the final ion exchange chromatography step (IEC), the purity of the protein was at least 95%. The types of the resins used for the affinity, ion exchange and gel filtration steps used in the method described here can be replaced with other resins of similar characters. The purification methods described here are depiction of examples of the purification strategy used for the preparation of TNK for the treatment of AIS, and are not limited by the use of types of chromatographic resins disclosed as other similar separation media may be used equally effectively. The bulk TNK was stored at a concentration of about 5 mg/mL at −80° C. [Examples 4, 5 and 7].

TABLE A

Increase in purity of TNK

| Chromatography Step | Amount of TNK/ML | % Purity of TNK |
|---|---|---|
| Harvest | 10 µg | ~80% |
| DAC-1 | 0.5 mg | ~90% |
| LAC-2 | 2 mg | ~92% |
| IEC-3 | 5 mg | >95% |

In the fourth part, various formulations of the bulk TNK solution were prepared in the range from 0.10 to 0.24 mg/mL per 10-mL vial in lyophilised form. In one type of the formulations, the ratio of the components was 1 part of TNK, 11 parts of L-arginine, 3.4 parts of phosphoric acid and 0.086 parts of polysorbate-20 as lyophilised powder. These formulations were subjected to the routine tests and were used in the clinical assessment of TNK for the treatment of AIS [Example 6].

In the fifth part, clinical testing and efficacy of the TNK formulations in the treatment of AIS was assessed in a multi-centric, open-label study involving about 35 affected subjects. From the data obtained in this study the safe and effective amount of TNK required for the treatment of AIS was obtained [Example 8].

The invention detailed above is illustrated with the following examples for the purpose of showing the utility of the invention. Embodiments below do not restrict the invention in any way from broader applications for preparation of compositions/formulations of the proteins similar to TNK. The teaching of this invention can also be used in the preparation of the proteins that are tPA analogues. The figures are illustrative and do not limit the broader application of the invention with regard to the quality and purity of the protein prepared and formulated.

EXAMPLES

Example 1: Molecular Biology, Biochemistry and Analytical Methods

The general molecular biology, biochemistry and analytical methods used during the procedures are known in the art. Routine techniques can be anticipated and are not described as they are available in public literature. The strains used as the bacterial host cells were derived from *E. coli* K-12 and the plasmids and DNA elements used for the preparation of expression vectors were retrieved from commonly available plasmids or designed and synthesised in-house and integrated to create required elements. The peptide sequence used for the preparation of artificial TNK gene is the native human tPA sequence having the amino acid changes as: Thr103Asn, Asn117Gln, Lys296Ala, His297Ala, Arg298Ala and Arg299Ala [MDAMKRGLCCVLLLC-GAVFVSPSQEIHARFRRGARSYQVICRDEKTQMIY-QQHQSWLRP VLRSNRVEYCWCNSGRAQCHSVPVK-SCSEPRCFNGGTCQQALYFSDFVCQCPEGFAGKCCE IDTRATCYEDQGISYRGTWSTAESGAECTNWNS-SALAQKPYSGRRPDAIRLGLGNHNYCRNPD RDSKP-WCYVFKAGKYSSEFCSTPACSEGNSDCYFGNGSAY-RGTHSLTESGASCLPWNSMILIG NVYTAQNPSAQALGLGKHNYCRNPDGDAKPWCHV-LKNRRLTWEYCDVPSCSTCGLRQYSQP QFRIKGGL-FADIASHPWQAAIFAKHRRSPGERFLCGGILISSCWIL-SAAHCFQERFPPHHLTVI LGRTYRVVPGEEEQKFEVEKYIVHKEFDDDTYDNDI-ALLQLKSDSSRCAQESSVVRTVCLPPA DLQLPDWTE-CELSGYGKHEALSPFYSERLKEAHVRLYPSS-RCTSQHLLNRTVTDNMLCAGDT RSGGPQANLHDACQGDSGGPLVCLNDGRMTLVGI-ISWGLGCGQKDVPGVYTKVTNYLDWIR DNMRP (SEQ ID NO: 1)]. All the subsequent synthetic DNA elements were based on this sequence and integrated into the cloning and mammalian expression vectors using standard methods. To confirm the identity and integrity of these elements, DNA sequencing was performed and sequences curated manually.

Example 2: Preparation of a Mammalian Cell Line for the Expression of TNK

An artificial TNK DNA sequence of human tPA gene with the above six mutations was artificially synthesised. This sequence was cloned in a plasmid vector having the elements for the efficient overexpression of the protein in Chinese Hamster Ovary (CHO) cells as a secreted protein in the medium. In the vector, the CMV enhancer/promoter element was followed by the TNK artificial gene followed by an SV40 polyA transcription termination element. The same plasmid also expressed the DHFR gene controlled by SV40 early promoter and SV40 polyA terminator as a separate cistron. The DHFR gene was also used as the expression marker in the recombined CHO cells for detection of TNK positive cells. The vector was transfected into the dihydrofolate reductase (DHFR) negative CHO cell line (DUKxB11) and genomically integrated stable clones with robust expression of secreted TNK were isolated. The expression levels of the TNK in various selected clones was tested with Western blot and SDS-PAGE analyses, followed by quantitative RT-PCR methods to establish the cell lines with stable and robust expression of the protein. One cell line with a good productivity of TNK was used to create the master cell bank, from which working cell bank was prepared and was used in the large-scale perfusion fermentation upstream processes. The TNK secreted by each clone was tested for the integrity and quality of the protein; also tests were performed to determine the enzymatic activities associated with this protein as per pharmacopoeia standards for medicinal applications.

Example 3: TNK Overexpression in CHO Cells

The TNK amino acid sequence was expressed under the control of CMV promoter/enhancer constitutive expression system in CHO cells. Here a new continuous fermentation technology called perfusion bioreactor was employed for the large-scale production of the protein. The TNK producing CHO cells were grown in the IMDM medium [INVITROGEN] with foetal bovine serum (FBS). From a culture of about $1\times10^6$ recombinant cells, final amount of about 6-12×$10^9$ cells were achieved with serial amplification of the cells in tissue culture flasks and roller bottles over a period of several days. The culturing conditions maintained at all steps during cell mass generation were: temperature: 36.5° C., $CO_2$: 5% and FBS: 10%. The confluence of the cell was maintained at >90% of the growing surface area in the flasks and bottles at all steps before harvesting of the cells for the next step. Periodic microscopy and biochemical tests were performed to detect the health and integrity of the growing cells. Then they were removed with mild trypsin treatment for transfer to the bioreactor, which was equipped with pH and DO probes and the cell supporting media in the core of the reactor to hold the cell in the reactor. The sterilised 5-L reactor was then inoculated with 6-12×$10^9$ cells and allowed to run for 3-4 day at glucose concentration of about 1-2 gm/L. This process led to the settling of the cells in the reactor in healthy conditions. Reactor parameters were: temperature: 36.6° C., aeration: 1.0 L/min, pH: between 7.2-7.4 [maintained using $CO_2$ and saturated sodium bicarbonate solution], agitation: 100 rpm, dissolved oxygen: 30%. Once the cells were placed in the support matrix, the medium was changed from IMDM with FBS to CHO-S-SFM II [INVITROGEN] without FBS. This medium was used throughout the product stage. At the start of the bioreactor phase, about 100 L of the initial media was harvested and discarded. Thereafter reactor temperature was kept at 33.5° C. during the production phase and about 100 L of the harvest collected every day while maintaining the reactor glucose level between 0.3-1.5 gm/L. In these conditions, the perfusion bioreactor can be run to collect up to 10,000 L of the harvest over a period of 3-4 months. The batches of harvested broth were filtered through 0.45 μm filters, collected in sterile containers and stored at 2-8° C. till further processed. The pools of harvested broth were periodically tested for the TNK content and sterility with established methods [FIGS. 1 and 2].

Example 4: Purification of TNK

Figure 1:
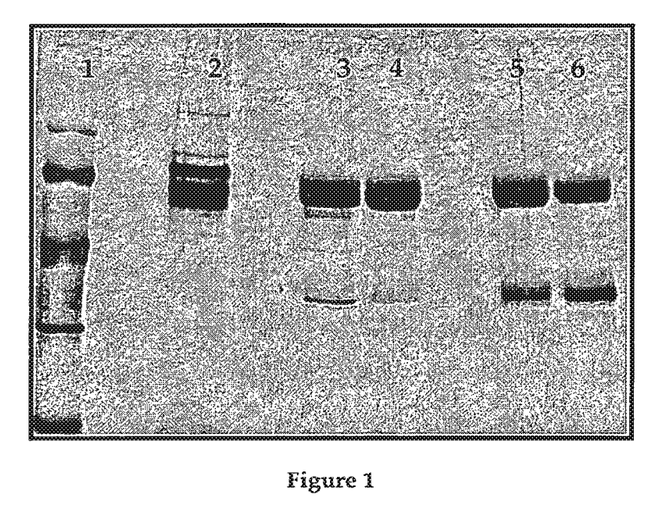
FIG. 1: Silver stained reduced SDS-PAGE gram of TNK content in purified fractions—1) molecular weight marker (from bottom: 21, 31, 45, 66, and 96 kDa); 2) harvested broth; 3) E-1 after DAC; 4) E-2 after LAC; 5) E-3 after IEC and 6) standard sample.
Figure 2:
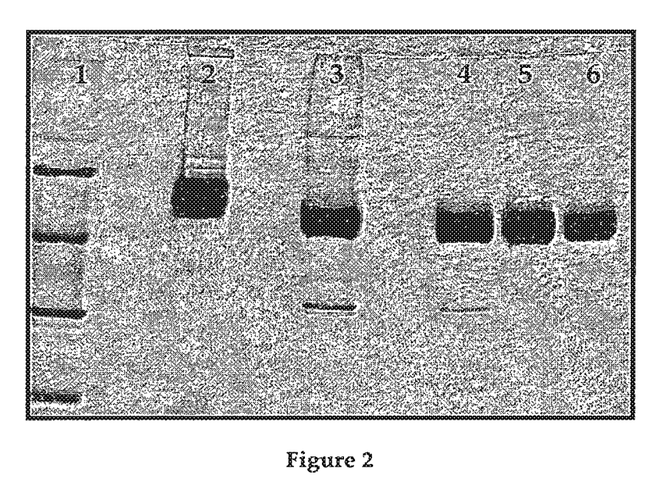
FIG. 2: Silver stained non-reduced SDS-PAGE gram of TNK content in purified fractions—1) molecular weight marker (from bottom: 21, 31, 45, 66, and 96 kDa); 2) harvested broth; 3) E-1 after DAC; 4) E-2 after LAC; 5) E-3 after IEC and 6) standard sample.
Figure 3:
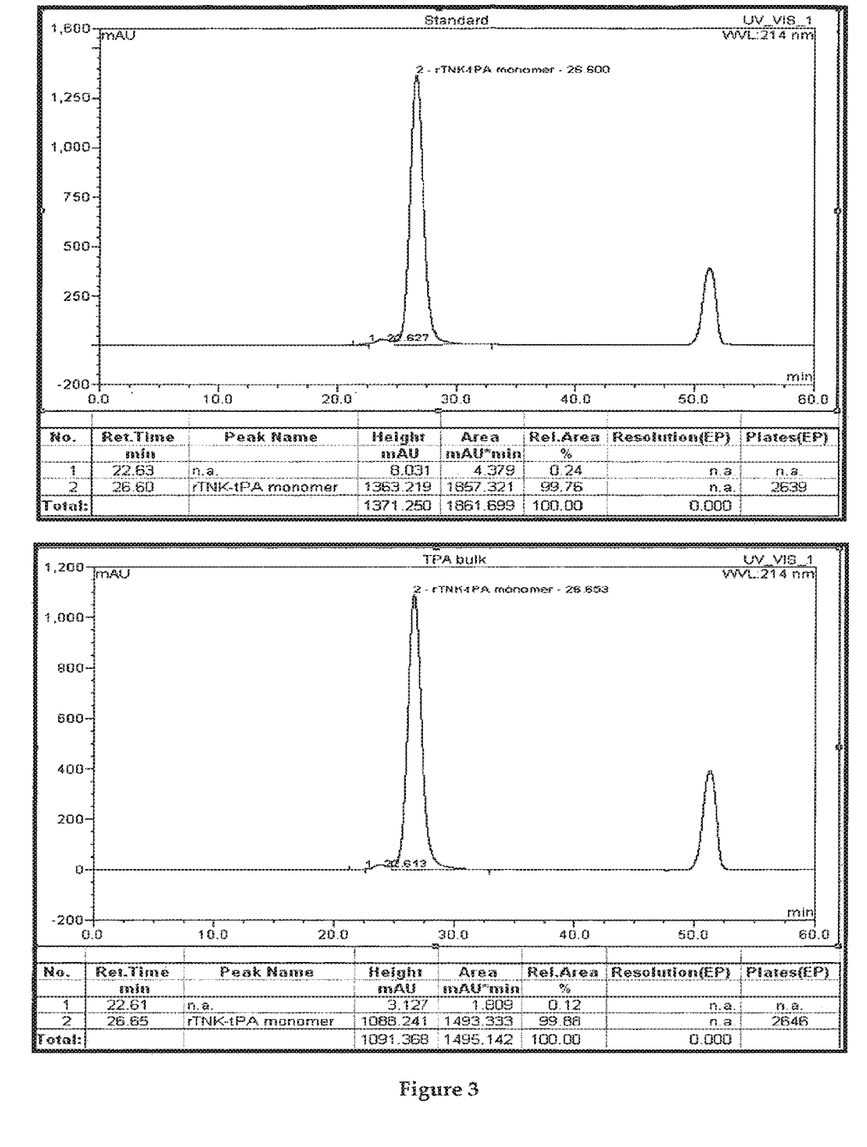
FIG. 3: An illustrative HPSEC graph of non-reduced TNK after chromatographic final step: TNK peptide (retention time: 26.653 min.) is more than 99% pure.

The batches of harvested broth were tested for the TNK content, its integrity and sterility [FIGS. 1 and 2]. In a single 1000-L batch for purification, a series of chromatography steps was used. In the first step, a batch of about 1000 L harvested broth with TNK content of about 10 mg/L was loaded on to a fast liquid chromatography (FLC) system column (300 mm×500 mm) with 11 L of activated dye affinity resin (Blue Sepharose 6 FF resin; GE Healthcare). The column was equilibrated with equilibrium buffer-1 (EB-1, sodium phosphate: 20 mM, NaCl: 0.15 M, pH 7.2) by passing 2 column volumes (CVs) at a flow rate of about 100-150 cm/h. The harvest was loaded onto the column with a linear flow rate of about 100-150 cm/h, followed by passing EB-1 of 2 CVs at a flow rate of about 100 cm/h. This was followed by 2-3 CVs of the wash buffer (WB-1, sodium phosphate: 20 mM, NaCl: 2 M, pH 7.2) at a flow rate of 100-150 cm/h. The bound target protein was eluted by passing about 4 CVs of elution buffer-1, (EUB-1, sodium phosphate: 20 mM, NaCl: 1 M, urea: 3 M, pH 7.2) and collected based on the absorbance at 280 nm. The eluate (E-1) was analysed for protein quantity and purity by SDS-PAGE electrophoresis. At this step, the TNK content in the total protein is about 90%. In the second step, buffer was exchanged using gel filtration chromatography. E-1 was loaded on to a column (300 mm×750 mm) with 25 L of gel filtration resin (Sephadex G-25). The column was then washed with 2 CVs of the exchange buffer (sodium phosphate: 20 mM, pH 7.2) with a linear flow rate of about 100-150 cm/h, and the eluate (E-2) was collected in a sterile container. In the third step, E-2 was loaded onto a column (200 mm×500 mm) with 4.5 L of activated L-lysine affinity resin (Lysine HyperD resin; Pall Corp.). The column was then equilibrated with equilibrium buffer-2 (EB-2, sodium phosphate: 20 mM, polysorbate-20: 0.043%, pH 7.2) by passing 2 column volumes (CVs) at a flow rate of about 100-150 cm/h, followed by passing 2 CVs of WB-2 (sodium phosphate: 20 mM, NaCl: 1 M, polysorbate-20: 0.043%, pH 7.2) at a flow rate of about 100 cm/h. The bound target protein was eluted bypassing 2 CVs of elution buffer-2 (EUB-2, arginine: 0.5 M, EACA (epsilon-aminocaproic acid): 0.2 M, polysorbate-20: 0.043%, pH 7.8 adjusted by phosphoric acid) and collected based on the absorbance at 280 nm. The eluate (E-3) was analysed for protein quantity and purity by SDS-PAGE electrophoresis [FIGS. 1 and 2]. At this step the TNK content of the total proteins is more than 95%. This was followed by buffer exchange by GFC to bulk storage buffer (L-arginine: 55 g/L, phosphoric acid: 17 g/L, polysorbate-20: 430 mg/L, pH 7.6±0.2). The final concentration of TNK in the solution was about 2 mg/mL, and the solution stored frozen till further use. This TNK solution was further concentrated using an anion exchanger resin (Capto Q resin, GE Healthcare) to 5 mg/mL before the formulations preparation.

Example 5: Analytical Assays

Figure 4:
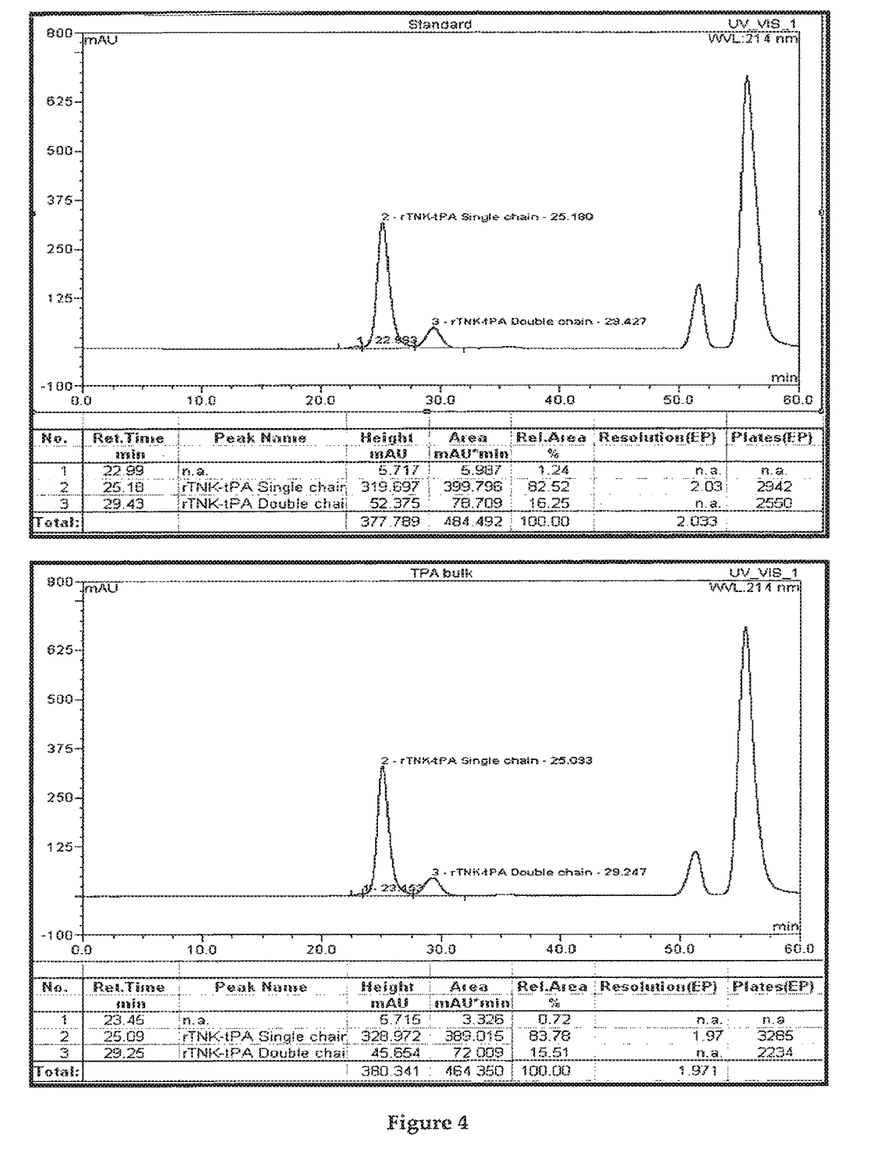
FIG. 4: An illustrative HPSEC graph of reduced TNK after chromatographic final step: TNK peptide, single chain (retention time: 25.093 min.) and TNK peptide, double chain (retention time: 29.247 min.).

During the production and purification processes, the in-process content of TNK in samples was determined by standard reducing and non-reducing SDS-PAGE methods [FIGS. 1 and 2]. 10% SDS-PAGE gels were prepared and 50 μg of the protein sample loaded to each well. For the determination of single chain and monomer content of the samples, reducing and non-reducing HPSEC [high performance size exclusion chromatography] methods were used respectively. The columns used for the HPSEC methods were silica-based size exclusion chromatography column for 10-500 KDa molecule separation range [FIGS. 4 and 5]. Standard and test samples were run in identical analysis conditions. Periodic in-process bioactivity assay were also performed to monitor the quality and integrity of the protein.

Example 6: Formulations of TNK

The various formulations of TNK were prepared to test the safety and efficacy of the TNK in the treatment of AIS. The formulations were based of the ratios as 1 part of TNK, 11 parts of L-arginine, 3.4 parts of phosphoric acid and 0.086 parts of polysorbate-20 as lyophilised products. The concentration of the bulk TNK solution used for this preparation was 5 mg/mL of TNK. After mixing the components without any precipitating TNK in the solution, the formulations were freeze-dried to stable powdery forms. A set of lyophilised formulations with TNK strength ranging from 0.10, 0.14, 0.18, 0.20, and 0.24 TNK per ml per 10-mL vial when reconstituted with 10 mL water for injection were prepared, and stored at about 4° C. till further used. These test formulations were subjected to different tests and stability studies, and found to be comparable in content and its stability for over a period of one year. The lyophilized formulations when reconstituted with 10 mL sterile water for injection to gave the above mentioned amount of TNK per mL in clear solutions for testing in clinical tests.

Example 7: Bioassay of TNK

Figure 5:
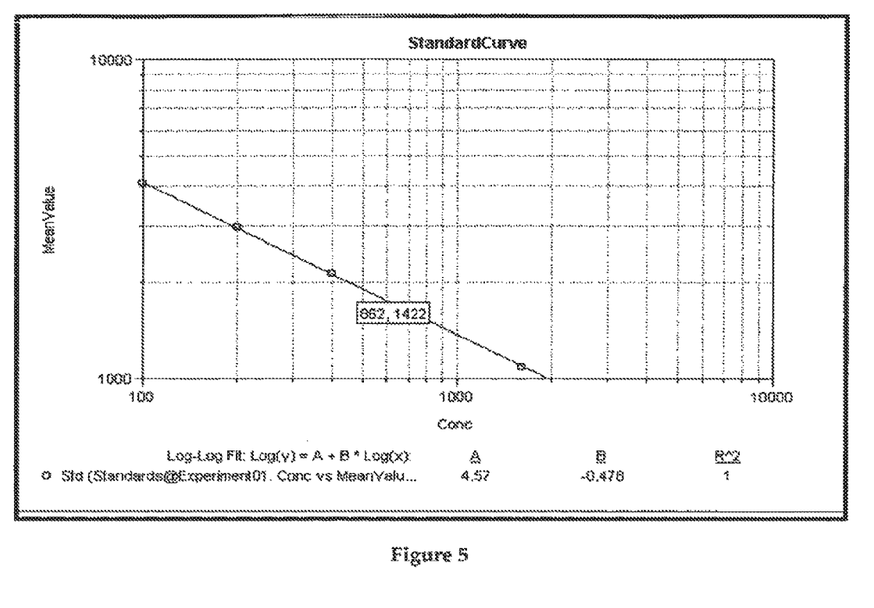
FIG. 5: An illustrative standard curve for the TNK bioactivity measurements.

The biological potency of the bulk and formulated TNK was determined by a rapid tubidimetric clot-lysis assay developed from the protocol of European pharmacopoeia monograph for alteplase. In a transparent 1.5-mL multi-well plate, 20 μL of human plasminogen (1 mg/mL) and 1 mL of human fibrinogen (2 mg/mL) solutions were taken, mixed and kept at 0° C. In a separate 1.5-mL multi-well plate, 0.5 mL of human thrombin (33 IU/mL) and 0.5 mL of test or reference TNK (1 mg/mL total proteins) solutions were prepared, mixed and brought to 37° C. All the dilutions were prepared with the solvent buffer as disclosed. 200 μL of reference/test mixes were added to the plasminogen/fibrinogen mixes and incubated at 37° C. After visibly turbid clot formation within 30 sec., bubbles subsequently formed in the tubes as clot lysis proceeded. The time points when thrombin mixes were added and the last bubble rise in the tube were recorded, which gave clot-lysis times in seconds. The clot-lysis times of test and reference TNK samples were determined and bioactivity test TNK batch calculated in international units (IU) per mL for the batch used in this example, accordingly to the EP protocol. FIG. 5 shows an illustrative standard curve for measurements of the TNK bioactivity. The bioactivity of the batch used here was 203 IU/mg. Tables B and C depict the numbers for the reference samples and test samples of TNK obtained in the clot-lysis bioactivity assay.

TABLE B

TNK bioassay: reference samples

| STD No. | Protein Conc. (ng/mL) of REF. STD. | Time (sec.) to clot-lysis for STD [avg. of 2] |
|---|---|---|
| 1 | 100 | 4078.29 |
| 2 | 200 | 2978.02 |
| 3 | 400 | 2139.05 |
| 4 | 800 | 1529.98 |
| 5 | 1600 | 1086.62 |

TABLE C

TNK bioassay: test samples

| Test Sample No. | Protein Conc. (ng/mL) of TEST Sample | Time (sec.) to clot-lysis for Sample [avg. of 2] | Calculated amount of TNK in Sample (ng/mL) using STD. curve |
|---|---|---|---|
| 1 | 100 | 3930.16 | 96.4 |
| 2 | 200 | 2970.70 | 199.5 |
| 3 | 400 | 2135.70 | 399.4 |
| 4 | 800 | 1538.90 | 804.7 |
| 5 | 1600 | 1091.50 | 1607.2 |

Example 8: Testing and Efficacy of the TNK Formulations

The clinical testing of the TNK formulations for AIS was performed using established methods used in clinical medicine. In a multi-centric, open label clinical trial on efficacy and safety of the TNK in the treatment of acute ischemic stroke (AIS) in subjects reporting within 4.5 hours of onset, two doses of TNK were used—0.1 mg/kg IV (intravenous injection) bolus and 0.2 mg/kg IV bolus in a randomized schedule. The TNK was injected as a bolus IV injection after confirmation of no intra-cerebral haemorrhage by CT scans over the period of 5-10 seconds. The dose of 0.1 mg/kg IV was received by 14 subjects and the dose of 0.2 mg/kg IV was received by 21 subjects. The NIH-SS (National Institute of Health Stroke Scale) was considered as the main efficacy parameter. In both the groups there was statistically significant improvement in the mean NIH-SS score within as early as 24 hours (Tables 1-3). This improvement was maintained at 7 days of assessment. The NIH-SS score improvement of ≥4 was considered as clinically significant improvement (Table 2). The 0.2 mg/kg group showed higher incidence of efficacy at this parameter at 24 hours (80.95%) which increased to 95.24% on Day 7. Although there was no statistically significant difference between the two dosage groups, this data suggested that the 0.2 mg/kg dose was preferable. Using the stricter criteria of NIH-SS score improvement of (Table 3), the 0.2 mg/kg group showed statistically significant increase in incidence of improvement at Day 7 (p=0.015) which confirmed that 0.2 mg/kg dose was preferable. The efficacy of TNK 0.2 mg/kg IV for NIH-SS >4 was seen in 80.95% subjects compared to 49.51% in the JACT study [Stroke 2006; 37(7):1810-5] with alteplase 0.6 mg/kg IV (p=0.0087), and 46.52% in the NINDS study [NEJM 1995; 333(24): 1581-87] with alteplase 0.9 mg/kg IV (p=0.0043), and 65.5% in an Indian study [Ann Indian Acad Neurol 2008; 11:221-4] with alteplase at 0.9 mg/kg IV (p=0.0172). These data showed that the dose of 0.2 mg/kg IV of TNK has significantly better efficacy than alteplase. As regards the stricter criteria of NIH-SS >8, TNK showed efficacy in 28.57% subjects which was numerically higher than the TNK 0.2 mg/kg data (24%) of Haley 2005 [Stroke 2005; 36: 607-612] and statistically non-significant compared to Haley 2010 [Stroke 2010; 41: 707-11] data (35.5%) with TNK 0.25 mg/kg. There were no symptomatic ICHs (intra-cerebral haemorrhage) in either group. Asymptomatic ICH was detected by CT scan at 48 hours in one subject in the 0.1 mg/kg group and in 2 subjects in the 0.2 mg/kg group. In total 3 (8.57%) asymptomatic ICH incidents were reported. The incidence of symptomatic or asymptomatic ICH has been reported to be 11.29% (=7/62) in Haley 2010 study and 20% (=10/50) in Haley 2005 study with TNK. Prior studies with alteplase had reported symptomatic ICH in up to 7% subjects and asymptomatic ICH in up to 31% subjects (NEJM 1995, 333, 24, 1581-7). The disclosed new data showed that the efficacy of the TNK to be better than that reported with alteplase in the treatment of AIS.

TABLE 1

Improvement in mean NIH-SS score

| | Study groups | | |
|---|---|---|---|
| | 0.1 mg/Kg N = 14 | 0.2 mg/Kg N = 21 | p value[#] |
| Baseline (Mean ± SD) | 10.07 ± 3.89 | 12.95 ± 5.08 | 0.081 |
| 24 hrs after injection (Mean ± SD) | 6.43 ± 4.65 | 5.90 ± 4.06 | 0.72 |
| 48 hrs after injection (Mean ± SD) | 5.57 ± 4.48 | 4.24 ± 3.97 | 0.31 |

TABLE 1-continued

Improvement in mean NIH-SS score

| | Study groups | | |
|---|---|---|---|
| | 0.1 mg/Kg<br>N = 14 | 0.2 mg/Kg<br>N = 21 | p value[#] |
| Day 7 after injection<br>(Mean ± SD) | 4.29 ± 4.23 | 3.20 ± 4.13 | 0.45 |
| p value compared<br>with baselins[@] | 0.0009 | <0.0001 | NA |

[#]p value, when compared between the groups; T test was applied.
[@]p value, when compared baseline and day 7 value within the group; T test was applied.
P < 0.05—statistically significant;
NA—Not applicable.
N = Number of patients

TABLE 2

NIH-SS improvement ≥ 4 points

| NIHSS<br>Improvement ≥ 4 | Study groups | | |
|---|---|---|---|
| | 0.1 mg/Kg | 0.2 mg/Kg | p value[#] |
| At 24 hrs<br>n (%) | 8 (57.14) | 17 (80.95) | 0.15 |
| At 48 hrs<br>n (%) | 10 (71.43) | 20 (95.24) | 0.133 |

TABLE 2-continued

NIH-SS improvement ≥ 4 points

| NIHSS<br>Improvement ≥ 4 | Study groups | | |
|---|---|---|---|
| | 0.1 mg/Kg | 0.2 mg/Kg | p value[#] |
| At day 7<br>n (%) | 11(78.57) | 20 (95.24) | 0.279 |
| p value[@] | 0.41 | 0.34 | NA |

[#]p value, when compared between the groups
[@]p value, when compared at 24 hrs and at day 7 value within the group
P < 0.05—statistically significant;
NA—Not applicable.
N = Number of patients
Fisher's Exact Test was applied for proportions.
n—Proportion of patients.

TABLE 3

NIH-SS improvement ≥ 8 points

| NIHSS<br>Improvement ≥ 8 | Study groups | | |
|---|---|---|---|
| | 0.1 mg/Kg<br>N = 14 | 0.2 mg/Kg<br>N = 21 | p value[#] |
| At 24 hrs<br>n (%) | 1 (7.14) | 6 (28.57) | 0.202 |
| At 48 hrs<br>n (%) | 2 (14.29) | 9 (42.86) | 0.136 |
| At day 7<br>n (%) | 2 (14.29) | 12 (57.14) | 0.015 |
| p value[@] | 1 | 0.118 | NA |

[#]p value, when compared between the groups
[@]p value, when compared data at 24 hrs and at 7 day value within the group
P < 0.05—statistically significant;
NA—Not applicable.
N = Number of patients.
Fisher's Exact Test was applied for proportions.
n—Proportion of patients.

We claim:

1. A method for treating acute ischemic stroke in a human subject in need thereof, the method comprising administering to the human 0.20 mg/kg body weight of tenecteplase as a single intravenous bolus injection, wherein the tenecteplase is produced by a process comprising expression in a mammalian cell line by a perfusion-based continuous fermentation process that provides at least 80% single-chain tenecteplase protein after purification.

2. The method of claim 1, wherein the bolus injection is given over not more than 10 seconds.

3. The method of claim 2, wherein the human is administered the tenecteplase within 6 hours of the onset of the acute ischemic stroke incident.

4. The method of claim 1, wherein the human is administered the tenecteplase within 6 hours of the onset of the acute ischemic stroke incident.

5. A method for treating acute ischemic stroke in a human subject in need thereof, the method comprising administering to the human 0.20 mg/kg body weight of tenecteplase as a pharmaceutical composition in a single intravenous bolus injection, wherein the pharmaceutical composition comprises (a) tenecteplase, (b) a pharmaceutically acceptable inorganic buffer, (c) a pharmaceutically acceptable stabilizing agent, and (d) optionally, a pharmaceutically acceptable carrier, where the tenecteplase is produced by a process comprising expression in a mammalian cell line by a perfusion-based continuous fermentation process that provides at least 80% single-chain tenecteplase protein after purification.

6. The method of claim 5, wherein the bolus injection is given over not more than 10 seconds.

7. The method of claim 6, wherein the human is administered the tenecteplase within 6 hours of the onset of the acute ischemic stroke incident.

8. The method of claim 5, wherein the human is administered the tenecteplase within 6 hours of the onset of the acute ischemic stroke incident.

9. The method of claim 5, wherein the buffer is phosphoric acid.

10. The method of claim 5, wherein the stabilizing agent is L-arginine.

11. The method of claim 5, wherein the stabilizing agent is a polysorbate.

12. A method for treating acute ischemic stroke in a human subject in need thereof, the method comprising administering to the human 0.20 mg/kg body weight of tenecteplase as a pharmaceutical composition in a single intravenous bolus injection, wherein the pharmaceutical composition comprises tenecteplase, phosphoric acid, L-arginine, and polysorbate, where the tenecteplase is produced by a process comprising expression in a mammalian cell line by a perfusion-based continuous fermentation process that provides at least 80% single-chain tenecteplase protein after purification.

13. The method of claim 12, wherein the bolus injection is given over not more than 10 seconds.

14. The method of claim 13, wherein the human is administered the tenecteplase within 6 hours of the onset of the acute ischemic stroke incident.

15. The method of claim 12, wherein the human is administered the tenecteplase within 6 hours of the onset of the acute ischemic stroke incident.

* * * * *